(12) United States Patent
Noro et al.

(10) Patent No.: US 7,212,659 B2
(45) Date of Patent: May 1, 2007

(54) APPARATUS FOR MEASURING BIOLOGICAL DATA AND EXERCISE MACHINES

(75) Inventors: Shinya Noro, Kyoto (JP); Takehiro Hamaguchi, Kyoto (JP); Takefumi Nakanishi, Kyoto (JP); Yasutaka Murase, Kyoto (JP); Susumu Minamikawa, Kyoto (JP)

(73) Assignee: Omron Corporation, Kyoto (JP)

( * ) Notice: Subject to any disclaimer, the term of this patent is extended or adjusted under 35 U.S.C. 154(b) by 788 days.

(21) Appl. No.: 10/408,191

(22) Filed: Apr. 3, 2003

(65) Prior Publication Data

US 2003/0190062 A1 Oct. 9, 2003

(30) Foreign Application Priority Data

Apr. 9, 2002 (JP) ............................. 2002-106739

(51) Int. Cl.
*G06K 9/00* (2006.01)
(52) U.S. Cl. ........................... 382/128; 382/115; 482/8
(58) Field of Classification Search ................ 382/107, 382/115, 116, 124, 126, 128, 129–133, 168, 382/172, 189, 209, 219, 274, 276, 305; 482/1, 482/4, 8; 600/300, 490, 520
See application file for complete search history.

(56) References Cited

U.S. PATENT DOCUMENTS

| | | | | |
|---|---|---|---|---|
| 5,474,090 A | * | 12/1995 | Begun et al. ................ 600/520 |
| 5,719,950 A | * | 2/1998 | Osten et al. ................. 382/115 |
| 5,730,124 A | * | 3/1998 | Yamauchi .................... 600/300 |
| 6,355,000 B1 | * | 3/2002 | Ogura ......................... 600/490 |
| 6,525,670 B1 | * | 2/2003 | Doi et al. .............. 340/870.16 |
| 6,561,951 B2 | * | 5/2003 | Cannon et al. ................. 482/1 |

FOREIGN PATENT DOCUMENTS

| | | |
|---|---|---|
| JP | 2000-126138 | 5/2000 |
| JP | 2001-258866 | 9/2001 |
| WO | 01/24700 | 4/2001 |
| WO | 01/59733 A2 | 8/2001 |
| WO | 01/59733 A3 | 8/2001 |

* cited by examiner

*Primary Examiner*—Matthew C. Bella
*Assistant Examiner*—Seyed Azarian
(74) *Attorney, Agent, or Firm*—Beyer Weaver LLP

(57) ABSTRACT

An apparatus for measuring biological data such as blood pressure of a user has a pulse detector for simultaneously obtaining fingerprint data and a first signal from the user's body such as a pulse wave signal. The fingerprint data are used to check if the user is a registered user. After the user's biological data such as pulse waves are measured and a second signal is obtained from the user, the first and second signals are compared to check if this is the same user from whom the fingerprint data were taken in order to prevent the apparatus from being used by a wrong person. Comparison may be made between the first signal and a pattern of pulse waves extracted from earlier obtained pulse waves stored in a memory. Similar components may be used for an exercising machine to prevent it from being used by a person not preliminarily registered or a person different from the one who passed the fingerprint test on the machine.

27 Claims, 13 Drawing Sheets

APPARATUS FOR MEASURING BIOLOGICAL DATA AND EXERCISE MACHINES

BACKGROUND OF THE INVENTION

This invention relates to apparatus for measuring biological data and to exercise machines. In particular, this invention relates to such apparatus and machines capable of checking whether or not the measured biological data and exercise data are indeed those of a right person.

Biological data such as blood pressure and body motion indicators as well as data on quantity of body motion which show results of body motion are adapted to be used in different fields as the user's individual data. Should a different person pretend to be the target person of whom biological data are intended to be taken and have such data actually taken, the consequence of such impropriety could be quite serious especially to the target person. In other words, it is very important to ascertain whether obtained biological data are indeed those of the target person whose data are being desired.

For this purpose, it has been known to store users' characteristic data in a memory area of an apparatus and to identify the user by referring to such stored characteristic data. There have been apparatus adapted to use a magnetic card or an IC card to identify the user before measuring his/her biological data or to have the user's ID inputted for identifying the user and then to measure his/her biological data. Such apparatus, however, cannot prevent a different individual from having measurements taken if the user's magnetic card or IC card has been stolen. There have also been apparatus adapted to identify the user by checking his/her fingerprints before allowing any biological data to be obtained but such apparatus cannot prevent a wrong individual from taking the place of the target person after the target person's fingerprint has been checked.

SUMMARY OF THE INVENTION

It is therefore an object of this invention in view of the problems described above to provide an apparatus for measuring biological data or data on the quantity of body motion capable of reliably ascertaining that the obtained data are indeed those of a specified target person.

An apparatus embodying the invention, with which the above and other objects can be accomplished, may be characterized as comprising data obtaining means for simultaneously obtaining fingerprint data and a signal (the "first signal") from the user's body, identifying means (the "first identifying means") for determining whether or not the user is one of preliminarily registered users by using the fingerprint data, measuring means for measuring biological data of the user (such as his/her pulse, blood pressure or athletic capability) and thereby obtaining another signal (the "second signal") from the user's body, another identifying means (the "second identifying means") for determining whether or not the user is the same user that was identified by the first identifying means by using the first signal and the second signal, and memory means for storing the biological data obtained by the measuring means. It may be characterized alternatively as comprising data obtaining means for simultaneously obtaining fingerprint data and a first signal from the user's body, first identifying means for determining whether or not the user is one of preliminarily registered users by using the fingerprint data, measuring means for measuring biological data of the user and thereby obtaining a second signal from the user's body, memory means for storing the biological data measured by the measuring means and the first signal, and second identifying means for determining whether or not the user is the same as the user identified by the first identifying means by using the first signal stored in the memory means and the second signal. It may additionally comprise abnormality identifying means for identifying an abnormal biological condition of the user by using the first signal stored in the memory means and the second signal obtained by the measuring means.

The second identifying means may conveniently identify the user by determining whether or not the first signal matches the second signal. The memory means may be adapted to store the measured biological data only if the first identifying means determines that the user is one of registered users and the second identifying means determines that the user is the same user identified by the first identifying means. The first signal and the second signal may be pulse wave data of the user. There may also be provided communicating means for transmitting the measured biological data to the memory means, as well as counter-measurement means for taking a specified countermeasure if the first identifying means determines that the user is not one of registered users or if the second identifying means determines that the user is not the same as the user identified by the first identifying means. Such counter-measurement means may serve to prevent the measuring means from taking the biological data of the user, and/or to output results of determination by the first identifying means or the second identifying means when an erroneous or fraudulent use is discovered.

It is further preferable to provide image taking means such as a camera such that the counter-measurement means can cause it to obtain an image of the user and/or an environment over 360 degrees around the measuring means, depending on the identification by the first identifying means or the second identifying means. The memory means may further serve to store this image obtained by the image taking means.

The counter-measurement means may be adapted to cause the fingerprint data obtained by the data obtaining means to be stored in the memory means if the first identifying means determines that the current user is not one of the preliminarily registered users.

An exercise machine embodying this invention may be characterized as comprising data obtaining means for simultaneously obtaining fingerprint data and a first signal from the body of a user using this exercise machine, first identifying means for determining whether or not the current user is one of preliminarily registered users by using the fingerprint data, exercising means for aiding the user to carry out exercises, obtaining exercise data on the amount of exercise carried out by the user and a second signal from the user's body and saving the exercise data, second identifying means for determining whether or not the current user is the same user identified by the first identifying means by using the first signal obtained by the first identifying means and the second signal obtained by the exercising means together with the exercise data, and memory means for storing the exercise data. Alternatively, the exercise data and the first signal may be stored in the memory means and the second identifying means may be adapted to determine whether or not the current user is the same user identified by the first identifying means by using the first signal stored in the memory means and the second signal obtained by the exercising means together with the exercise data.

Figure 13:
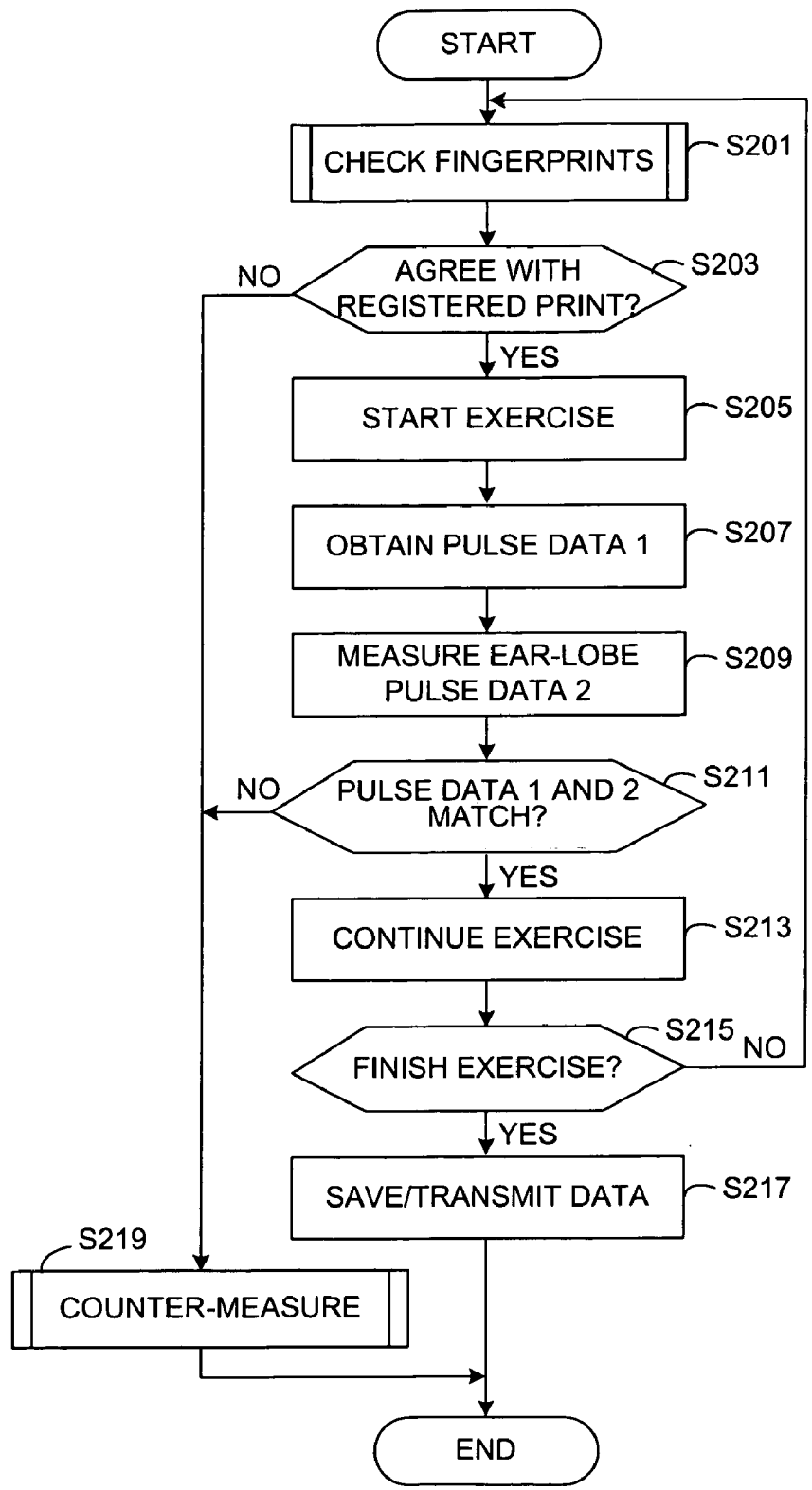
FIG. 13 is a flowchart of an operation program for the exercise machine of FIG. 11.
Figure 14:
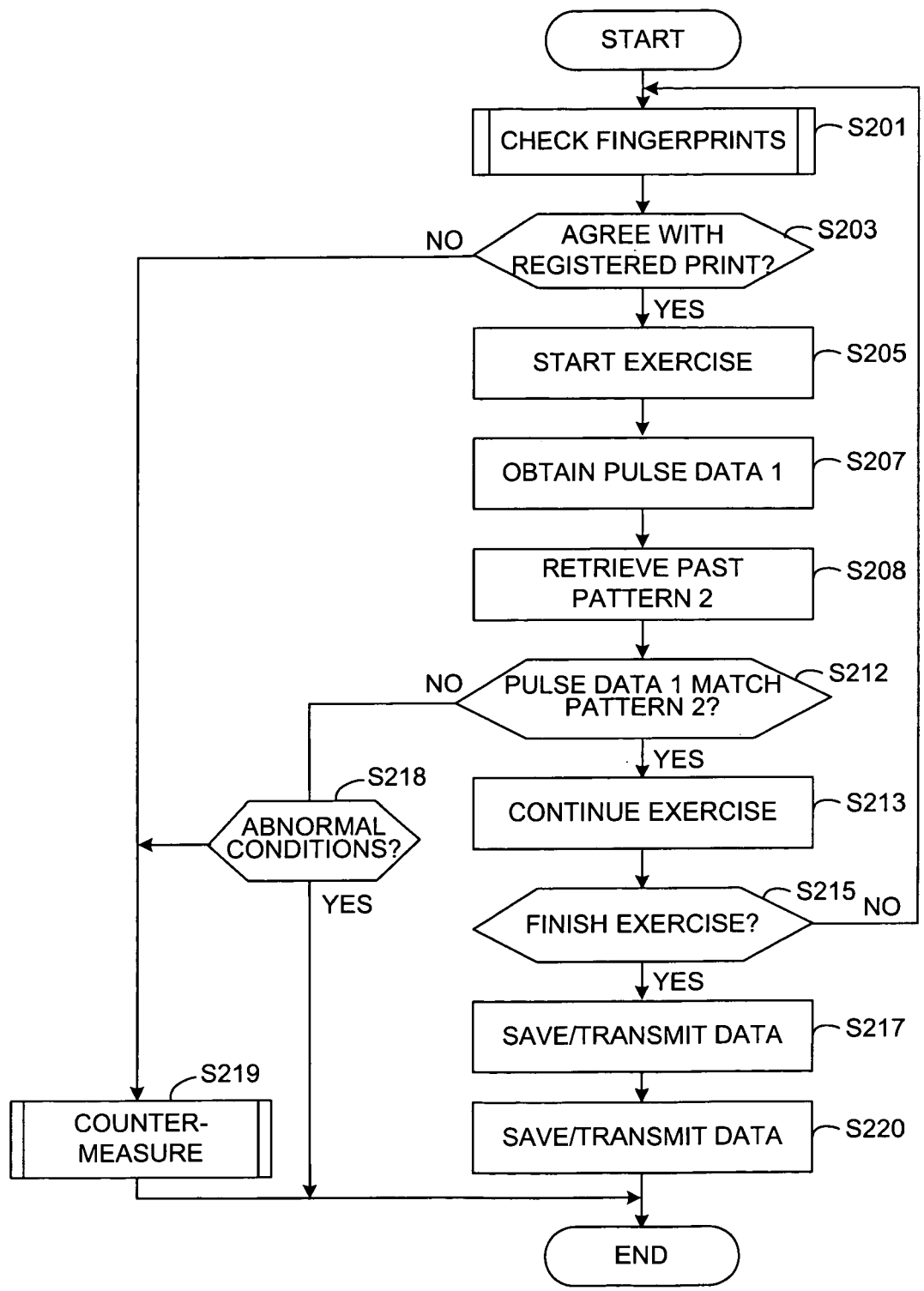
FIG. 14 is a flowchart of an operation program for another exercise machine which is a variation of the machine of FIG. 11.
Figure 15:
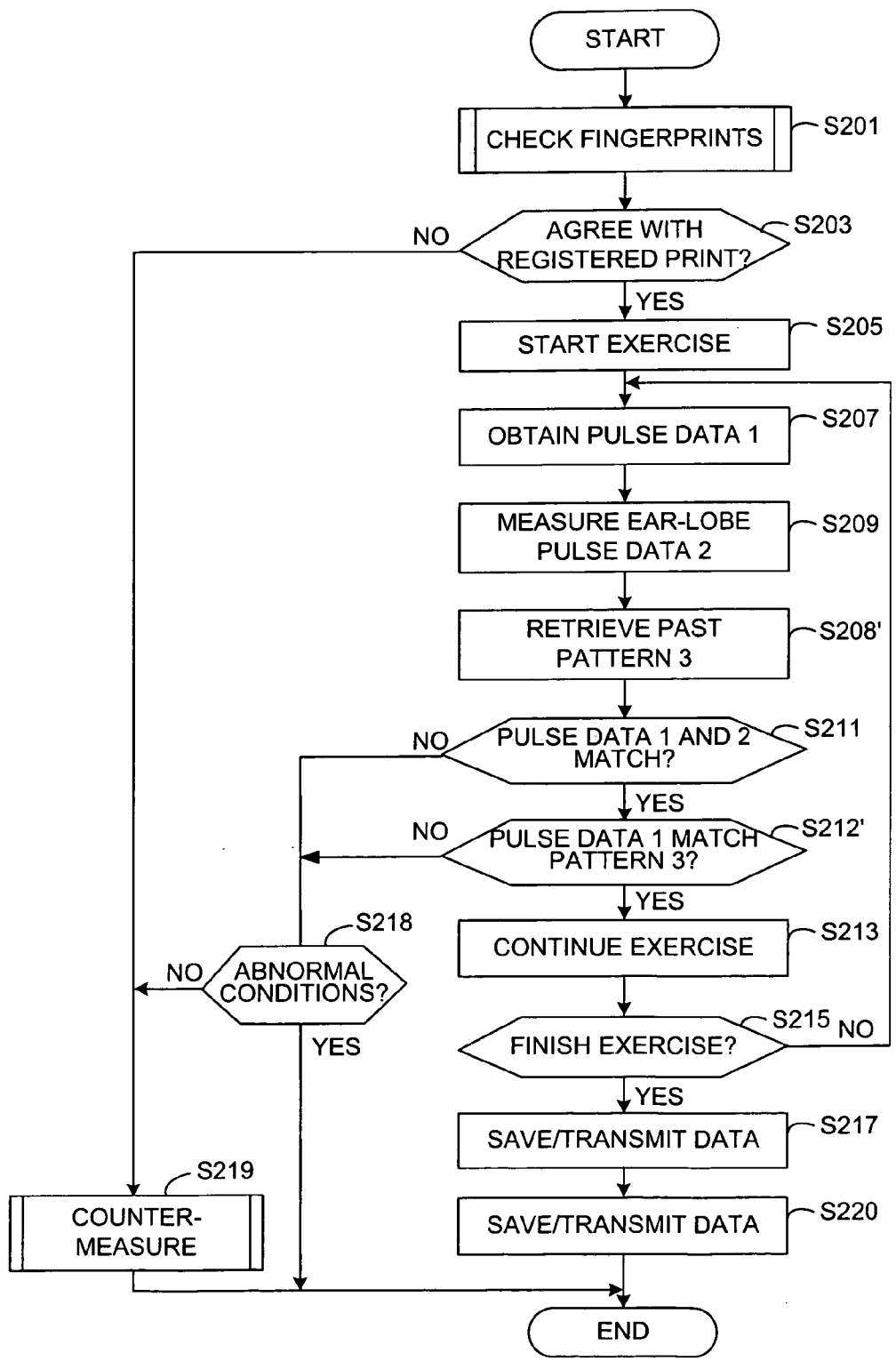
FIG. 15 is a flowchart of another operation program for the variation exercise machine.

Throughout herein, like or equivalent components are indicated by a same symbol even where they are components of different apparatus and may not necessarily be described repetitiously. Similarly, like or equivalent steps in the flowcharts of FIGS. 13, 14 and 15 are indicated by a same symbol although they are steps in different programs and may not necessarily be explained repetitiously.

DETAILED DESCRIPTION OF THE INVENTION

Figure 1:
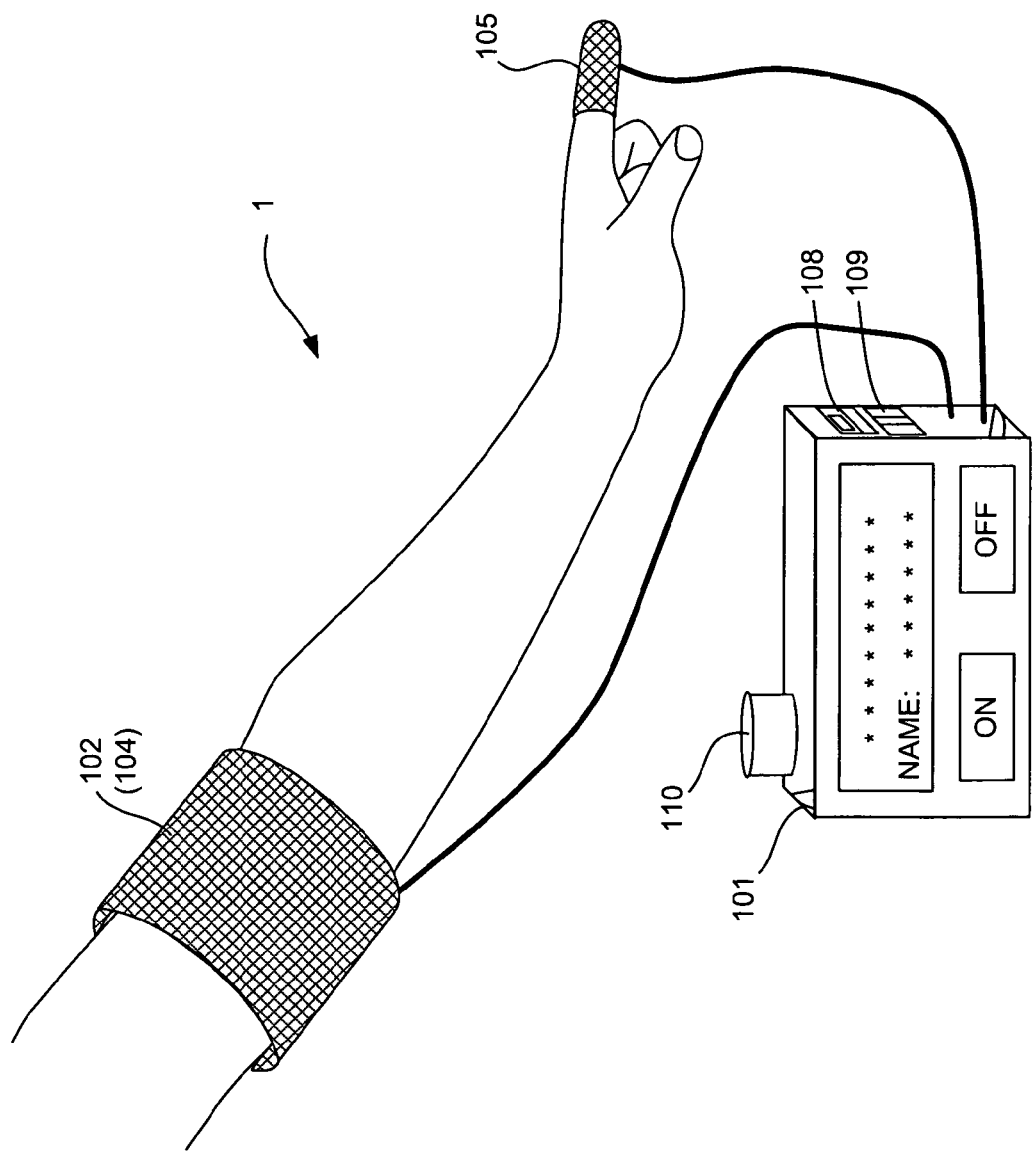
FIG. 1 is a schematic external view of a sphygmomanometer embodying this invention.
Figure 2:
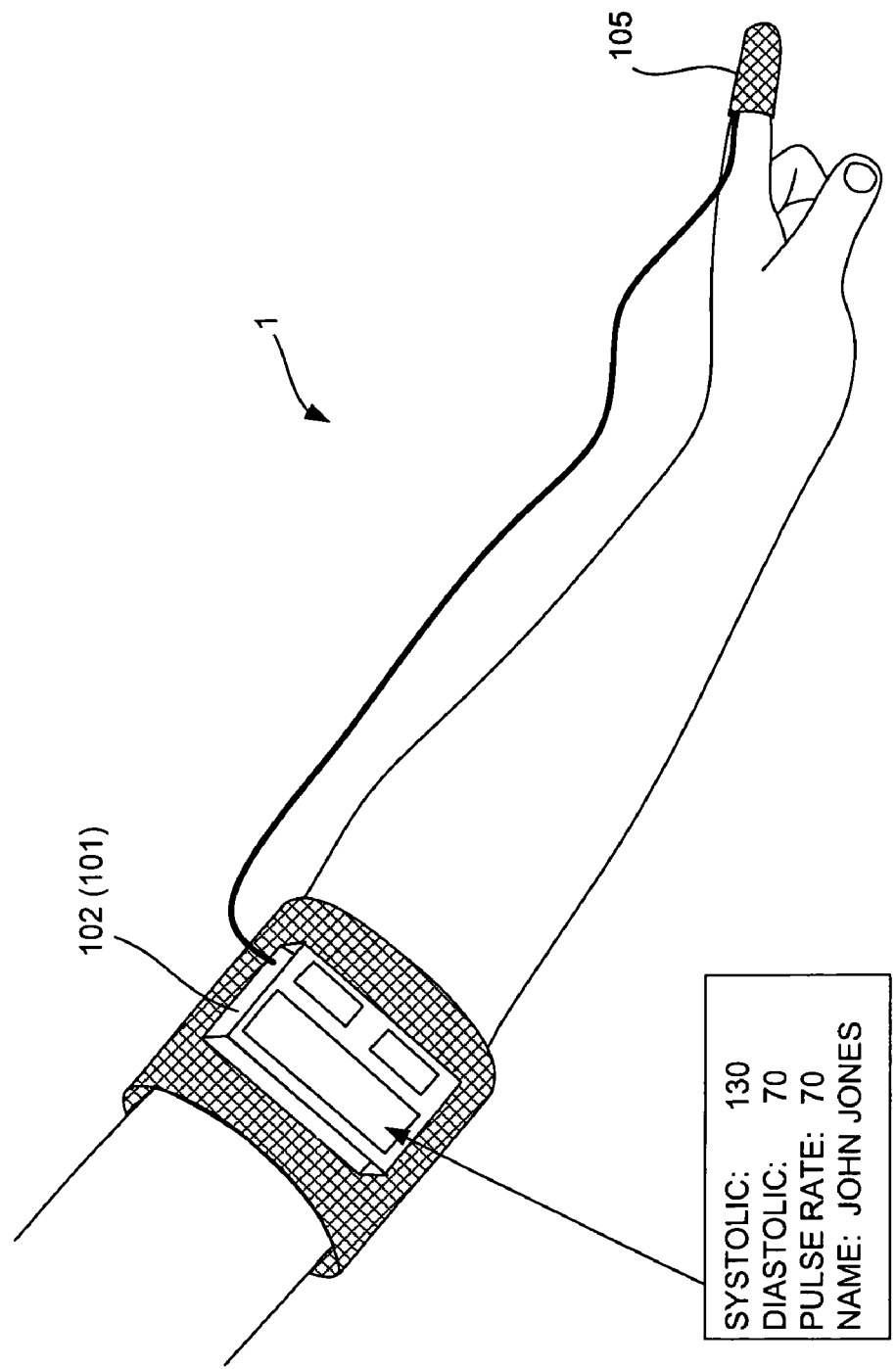
FIG. 2 is a schematic external view of another sphygmomanometer embodying this invention.

FIG. 1 shows a sphygmomanometer 1, as an example of apparatus embodying this invention for measuring biological data of a user's body, comprising a control unit 101 for controlling the overall operations of the apparatus, a blood pressure detector 102 for measuring the blood pressure of a patient (user) by means of a cuff 104, a fingerprint detector 105 for detecting the user's fingerprints, a microphone 108 serving as a voice input device, a speaker 109 serving as a voice output device, and a camera 110 for taking pictures of the environment. FIG. 2 shows another sphygmomanometer 1 embodying this invention characterized as having its control unit 101 and blood pressure detector 102 formed integrally.

Figure 3:
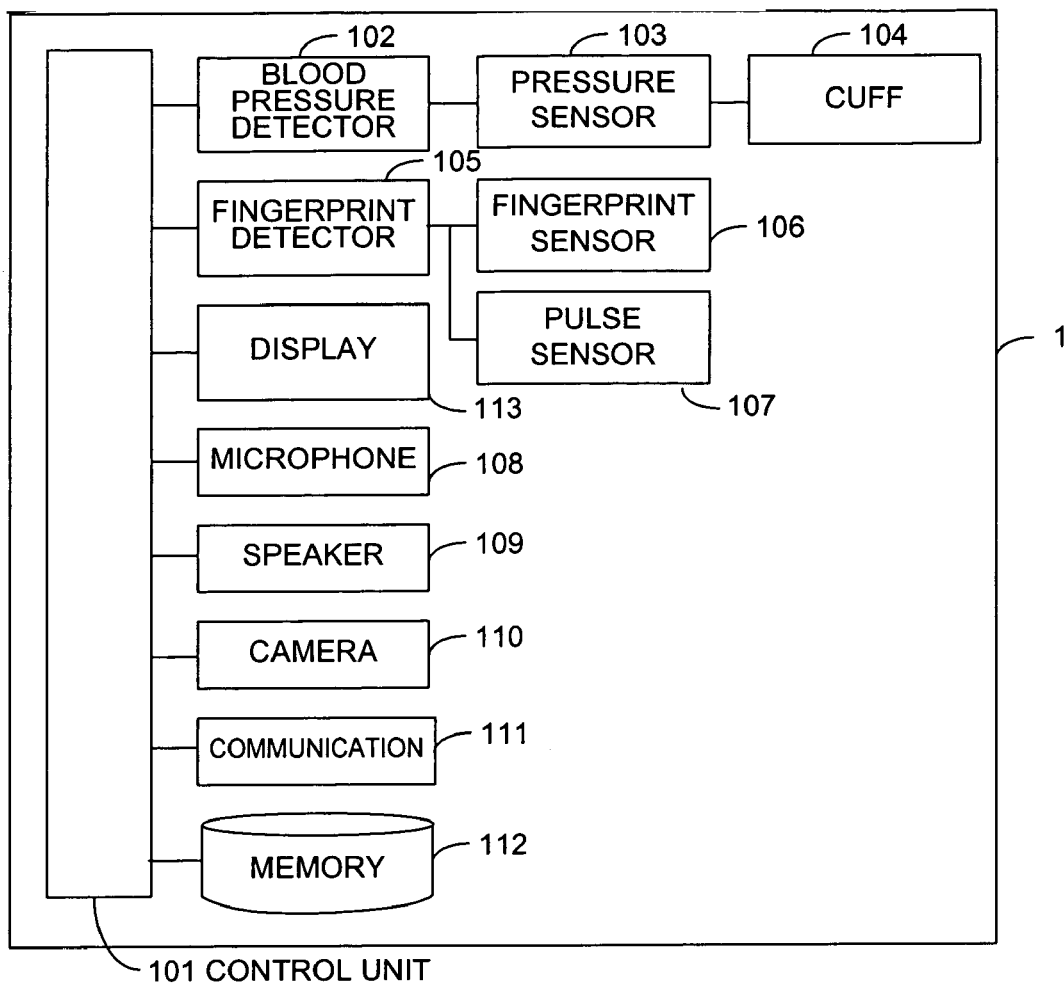
FIG. 3 is a block diagram for showing the control system of the sphygmomanometers of FIGS. 1 and 2.

As shown in FIG. 3 which is a block diagram of the control system of the sphygmomanometer 1 embodying this invention, the blood pressure detector 102 determines the blood pressure of the user based on outputs from a pressure sensor 103 placed in the cuff 104, and the fingerprint detector 105 not only recognizes the user's fingerprints on the basis of outputs from a fingerprint sensor 106 but also serves to measure the user's pulse waves on the basis of outputs from a pulse sensor 107. In addition to the microphone 108, the speaker 109 and the camera 110, as described above, a communication interface 111 for communicating with external apparatus, a memory 112 for storing various data and a display device 113 for displaying various data are also included as parts of the sphygmomanometer 1.

Figure 4:
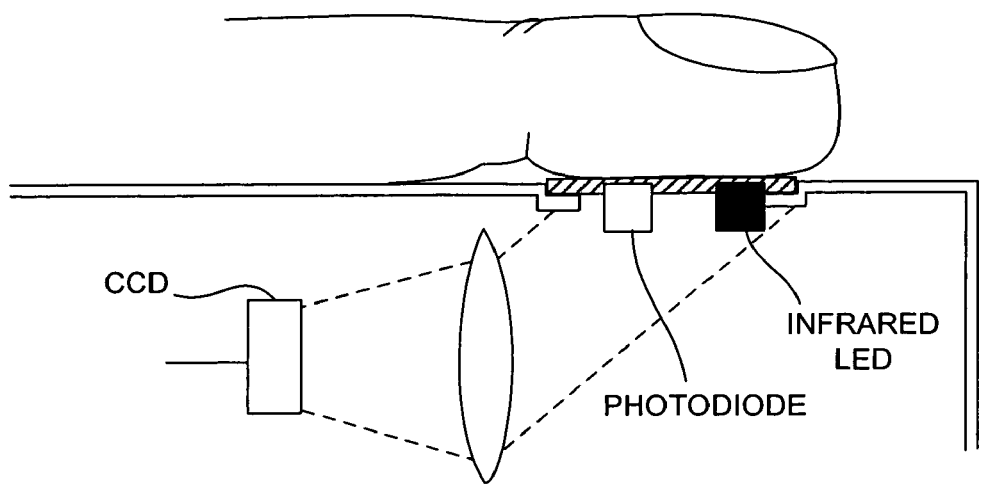
FIG. 4 is a schematic side view of the fingerprint detector.

The invention is not limited by the way in which the user's fingerprints and pulse rate are detected. Any known detection method may be utilized. FIG. 4 shows an example whereby light emitted from a light emitter such as an infrared light emitting diode is reflected by the user's finger and received by a light receiver which may comprise a photodiode. The reflected light from the finger is received by an image receiving element such as a charge coupled device CCD and the fingerprint sensor 106 detects the fingerprint by obtaining fingerprint data therefrom.

Figure 5:
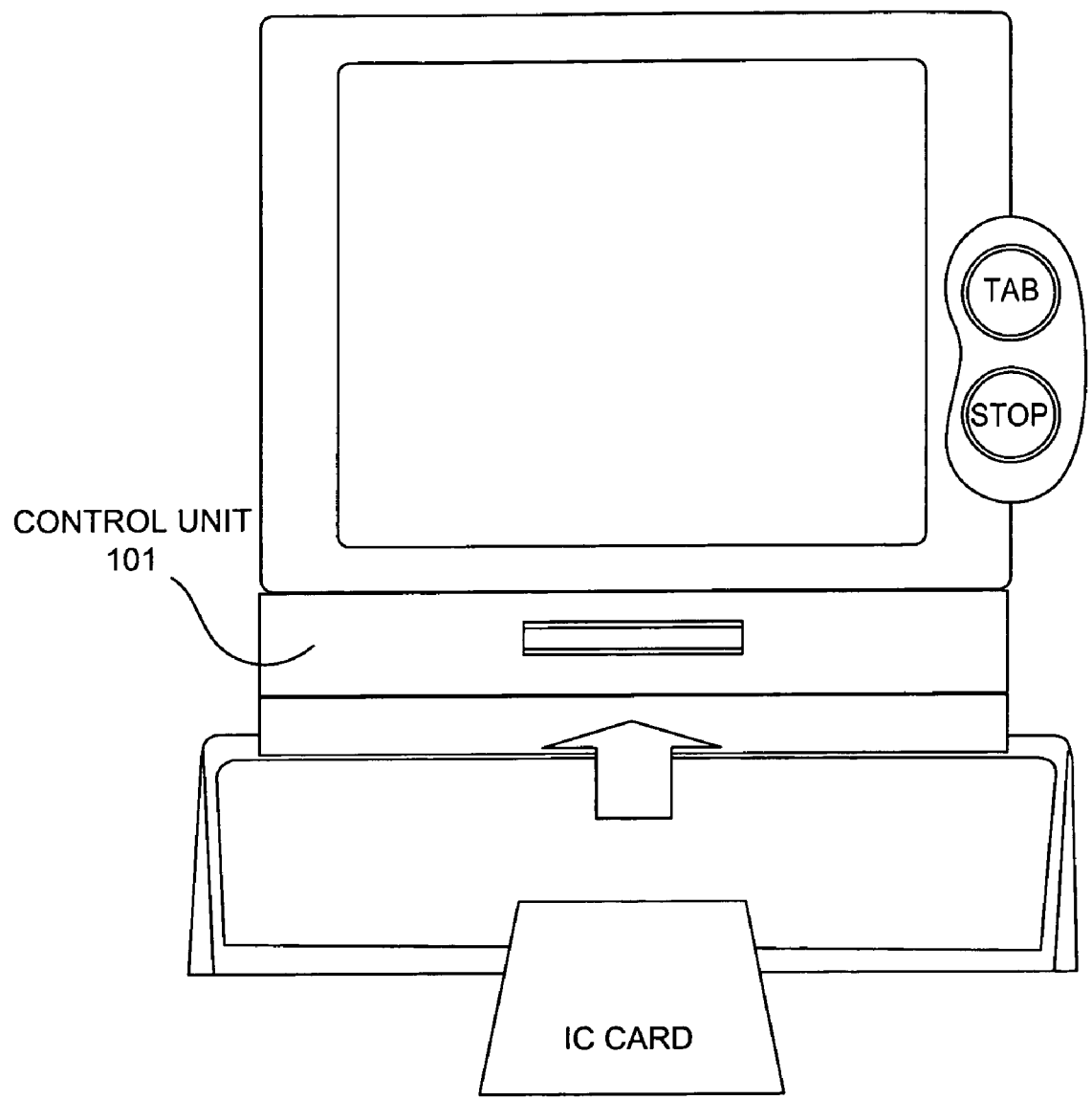
FIG. 5 is a front view of an example of the control unit.
Figure 6:
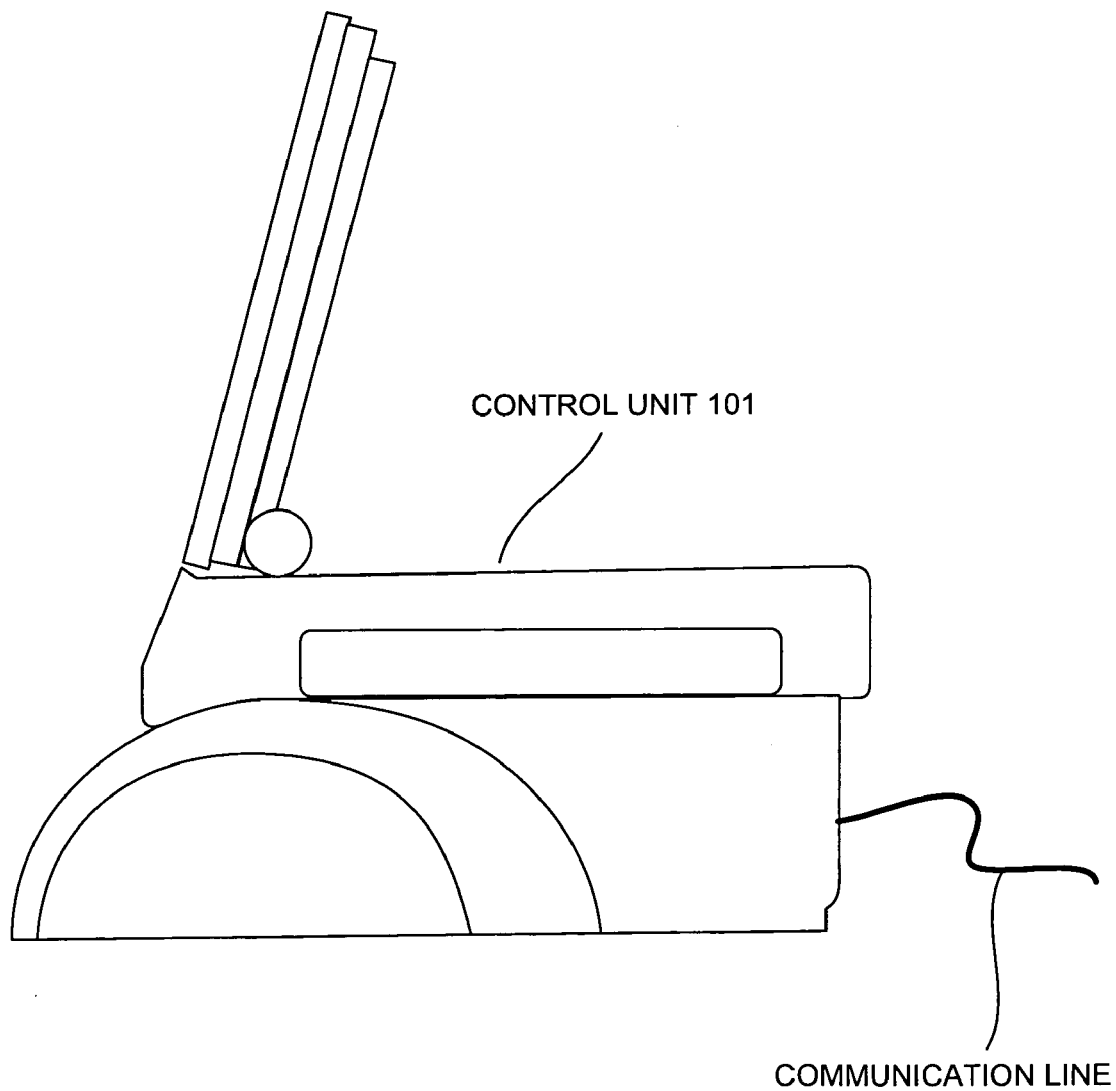
FIG. 6 is a side view of another example of the control unit.

The pulse sensor 107 detects the pulse wave on the basis of the optical data received by the light receiver. Explained more in detail, the pulse sensor 107 detects the pulse wave on the basis of the light reflected by the hemoglobin moving inside the blood vessels in the finger, The flow rate of the hemoglobin inside the blood vessels in the finger varies according to the rhythm of the blood pushed out of the heart. Thus, the intensity of the light reflected by the red hemoglobin also changes accordingly. The pulse sensor 107 detects the variations in the intensity of such reflected light to detect the user's pulse rate. Not every item of such data is required to be saved in the memory 112 shown in FIG. 5. Such data may be saved on an IC card, as shown in FIG. 5, apart from the main body of the sphygmomanometer 1 itself. Further alternatively, these data may be transmitted to an external memory device through the communication interface 111. FIG. 6 shows another example of the control unit 101 with a communication interface 111 comprising a network of telephone wires, dedicated lines, LAN or Internet. Data may be transmitted through a wireless means.

Next, flowcharts will be referenced to explain the operations of the sphygmomanometer 1 described above. It is presumed, however, that the user is one who has already registered his/her fingerprint data with the sphygmomanometer 1. The routine for registering one's fingerprint data is not a part of the present invention. The user's preliminarily registered fingerprint data may be stored in the memory 112 of the sphygmomanometer 1 or in a separate memory device, as explained above.

Figure 7:
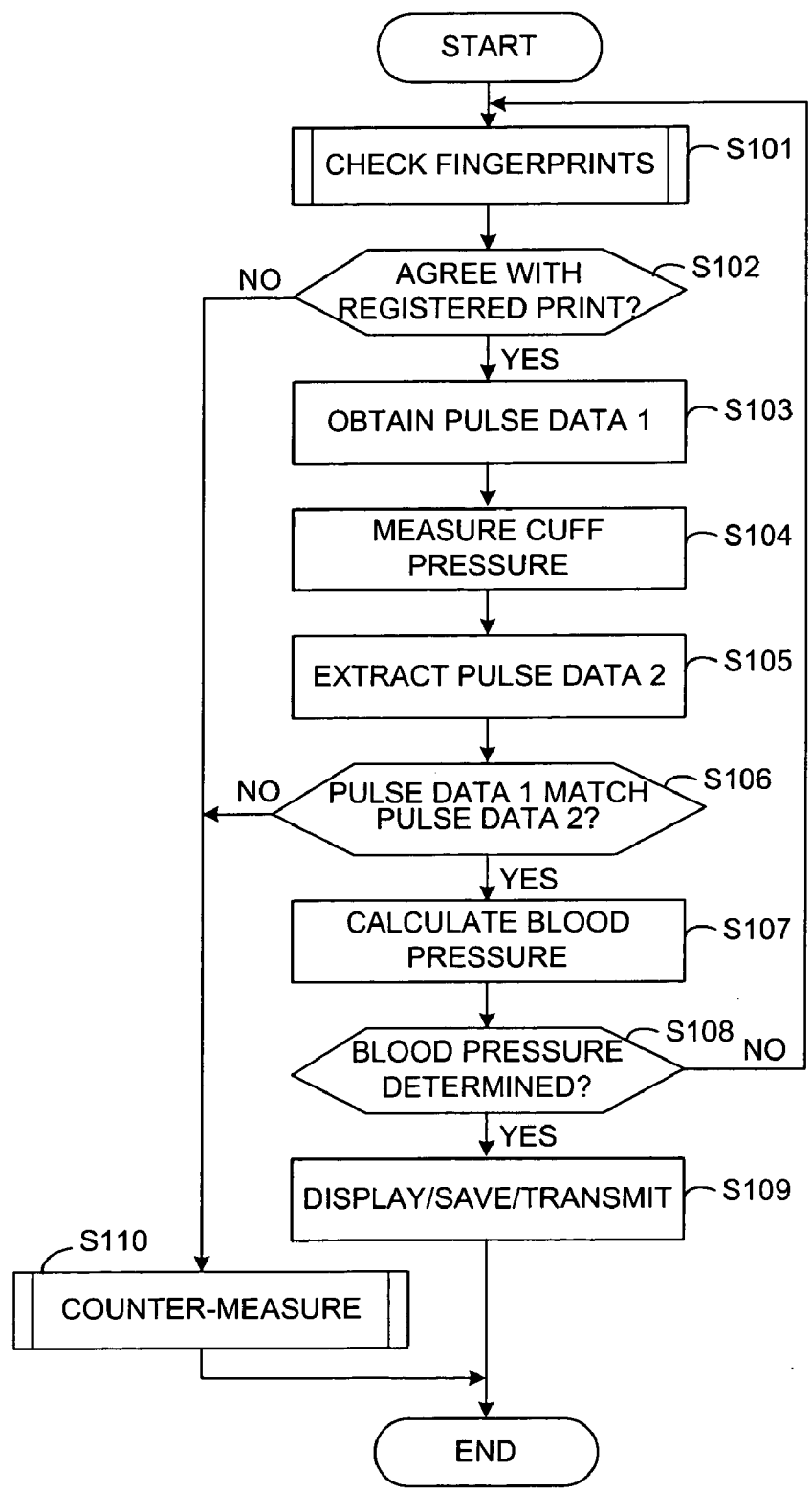
FIG. 7 is a flowchart of an operation program for the sphygmomanometer of FIG. 1.

FIG. 7 shows an example of a program to be retrieved from the memory 112 and executed by the control unit 101. The fingerprint of the user is examined by the fingerprint detector 105 with reference to data stored in the memory 112, or another memory, to determine whether or not it is the fingerprint of a preliminarily registered user (Step S101). This is a known routine and hence will not be described in detail.

If it is determined that the user is one of preliminarily registered users (YES in Step S102), pulse waves are detected by the pulse detector 105 and measured (Step S103). For the convenience of the description, the pulse wave data obtained in Step S103 are hereinafter referred to as "Pulse Data 1". Next, the pressure inside the cuff 104 is sensed by the pressure sensor 103 (Step S104) and pulse waves of the user are extracted on the basis of the measured pressure inside the cuff 104 (Step S105). The pulse wave data thus obtained in Step S105 are hereinafter referred to as "Pulse Data 2". Measurements for obtaining Pulse Data 1 and Pulse Data 2 may be repeated any number of times at specified intervals or within a specified length of time.

Next, Pulse Data 1 obtained in Step S103 and Pulse Data 2 extracted in Step S105 are compared (Step S106). If they agree (YES in Step S106), the user is identified as the same user earlier identified in Step S101 as the preliminarily registered user and his/her blood pressure is calculated on the basis of the pressure inside the cuff 104 measured in Step S104 (Step S107).

If the blood pressure has been calculated (YES in Step S108), the calculated blood pressure is displayed on the display device 113 and stored in the memory 112 (or somewhere else). If a communicating means is provided, it may be used to transmit data inclusive of the calculated blood pressure to an external apparatus or device (Step S109).

If the detected fingerprints in Step S101 do not match any preliminarily registered fingerprints (NO in Step S102), or if Pulse Data 1 obtained in Step S103 and Pulse Data 2 extracted in Step S105 do not match (NO in Step S106), it is concluded that the user is improperly using the sphygmomanometer 1, and a specified counter-measure is taken (Step S110). The counter-measure to be taken may comprise a display of a warning message on the display device 113 or the sounding of a warning from the speaker 109. When the improper use of the sphygmomanometer 1 is thus discovered, the camera 110 may be activated to photograph the user's face and to store the photographed image in the memory 112 or elsewhere. The camera 110 may be operated so as to photograph in all directions (over 360 degrees of angle) around the position of the sphygmomanometer 1. Moreover, the microphone 108 may be activated to record the voice during the relevant time interval and to store the recorded voice data. If the sphygmomanometer 1 is provided with a communicating means, such recorded image and voice data may be transmitted to any appropriate external apparatus or device.

The counter-measure may also include the process of inhibiting the use of the sphygmomanometer 1, say, by disabling it, or preventing the obtained blood pressure data from being stored and/or transmitted.

It may be so programmed that the aforementioned counter-measure is taken only after such disagreement (as in Steps S102 and S106) occurred for a specified number of times.

The counter-measure in the case of a user who simply has not registered himself/herself yet may include a process of suggesting that he/she should register himself/herself.

Figure 8:
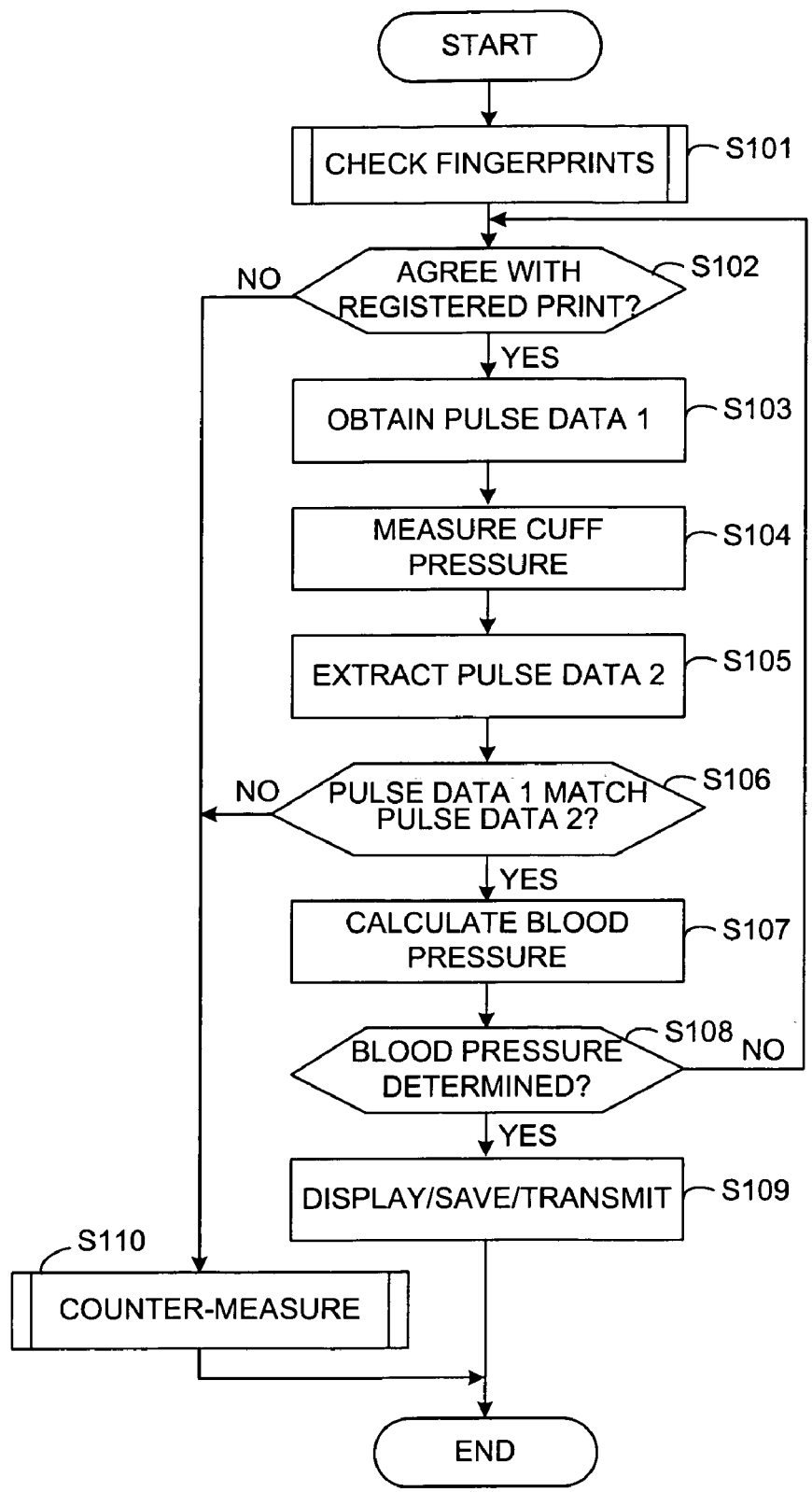
FIG. 8 is a flowchart of another operation process for the sphygmomanometer of FIG. 1.

If the blood pressure could not be calculated in Step S107 for whatever reason such as a measurement error (NO in Step S108), the program returns to Step S101 (as shown in FIG. 7) or to Step 102 (as shown in FIG. 8). In other words, the step of examining the user's fingerprints in Step S101 need not necessarily be repeated.

Both flowcharts in FIGS. 7 and 8 show that the calculation of blood pressure in Step S107 is carried out only after the user has been identified to be a correct person, but the program may be modified such that this calculation is carried out first and the calculated value is saved and/or transmitted only after the user is recognized.

Figure 9:
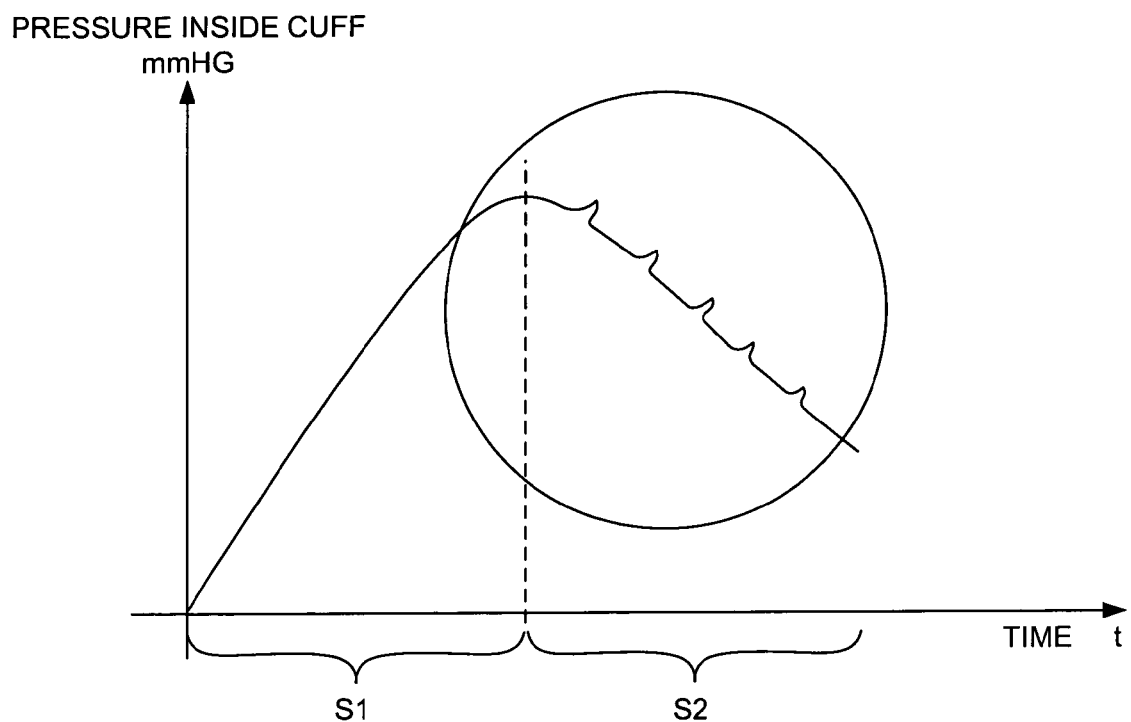
FIG. 9 is an example of a graph showing measured pressure inside the cuff.

The process of extracting pulse waves by means of the blood pressure detector 102 in Step S105 will be explained next more in detail. FIG. 9 shows an example of pulses measured inside the cuff 104 by the blood pressure detector 102 as a function of time. On the basis of the pressure thus measured inside the cuff 104, the systolic and diastolic values of the user are calculated in Step S107 of FIGS. 7 and 8. Since the method of this calculation is well known, it will not be explained here.

When the pressure inside the cuff 104 is measured in Step S104 of FIGS. 7 and 8, air is firstly pumped into the cuff 104 (Period S1 as shown in FIG. 9). As the air inside the cuff 104 is gradually removed, the pressure inside the cuff 104 decreases gradually (Period S2 as shown in FIG. 9). When the blood pressure of the user becomes higher than the pressure inside the cuff 104, the cuff 104 comes to be pressed from inside and the pulse wave of the user can be sensed by the pressure sensor 103. FIG. 9 indicates these instances by a circle.

Figure 10:
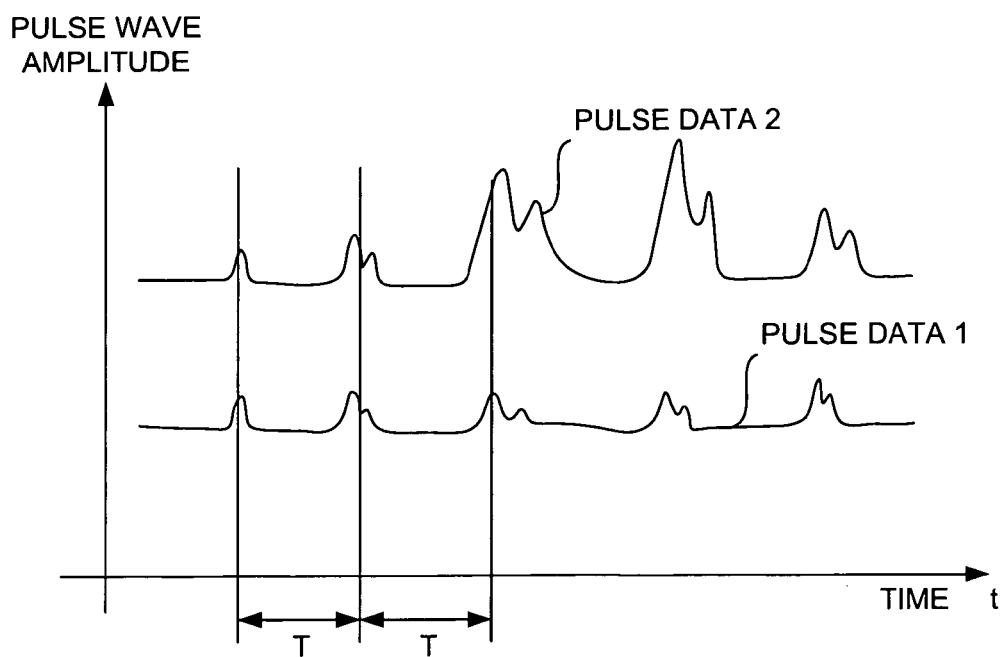
FIG. 10 is an example of a graph for comparing Pulse Data 1 and 2.

In Step S106 of FIGS. 7 and 8, Pulse Data 1 obtained in Step S103 and Pulse Data 2 extracted in Step S105 are compared, for example, as shown in FIG. 10, as a function of time. In FIG. 10, Pulse Data 2 are obtained by carrying out a specified correction process on the pulse waves extracted from the circled portion of FIG. 9 by means of the aforementioned blood pressure detector 102.

One way to compare Pulse Data 1 and Pulse Data 2 is to compare their periods. In other words, periods T are extracted from Pulse Data 1 and Pulse Data 2 as shown in FIG. 10 and since they are synchronized, it may be concluded that they are data taken from one and the same person. Pulse Data 1 and 2 may be compared in other manners. For example, their waveforms, the ratios at specified parts of their waveforms, or the phenomenon of so-called fluctuation contained in the waveforms may be compared.

In summary, the sphygmomanometer 1 thus structured according to this invention can dependably prevent an improper measurement of blood pressure of a wrong person because not only the user's fingerprints are taken to ascertain whether this is a preliminarily registered person but also care is taken to ascertain that the person being measured is indeed preliminarily registered, and use is made of two pulse waves which are necessarily extracted when the blood pressure is measured.

Although the invention was described above with reference to an example wherein pulse waves which represent the user's body impedance are used for measuring the blood pressure (as an example of biological data) and for ascertaining the registered status of the user, the user's body impedance may be used in any other form. Although the invention was described above with reference to an example wherein it is the user's blood pressure that is measured as an example of his/her biological data, the invention is equally applicable to the measurement of the user's other biological data such as the blood sugar content. As a further example, the present invention is applicable when the user's athletic capability is measured as his/her biological data.

Figure 11:
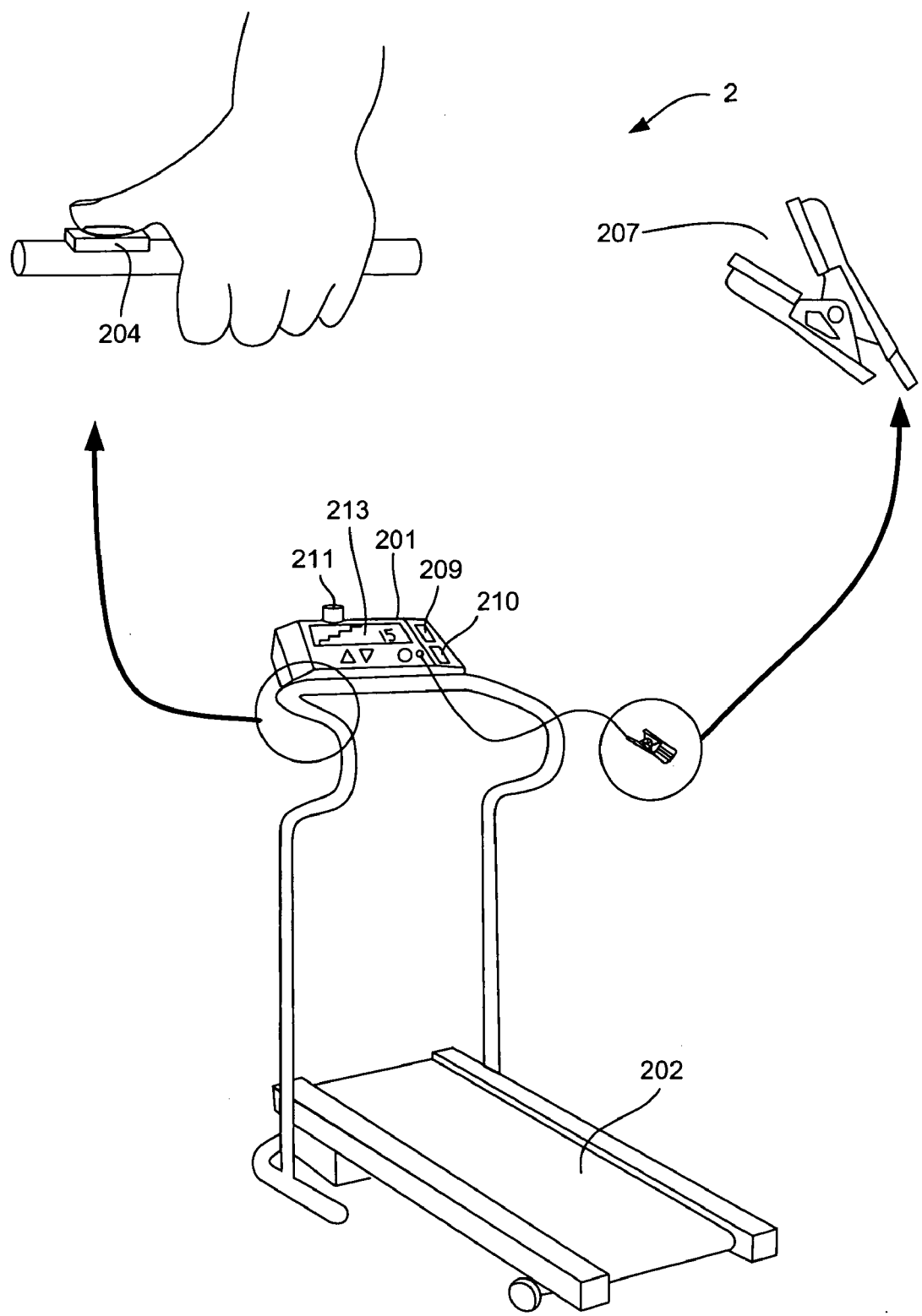
FIG. 11 is an external view of an example of exercise machine embodying this invention.
Figure 12:
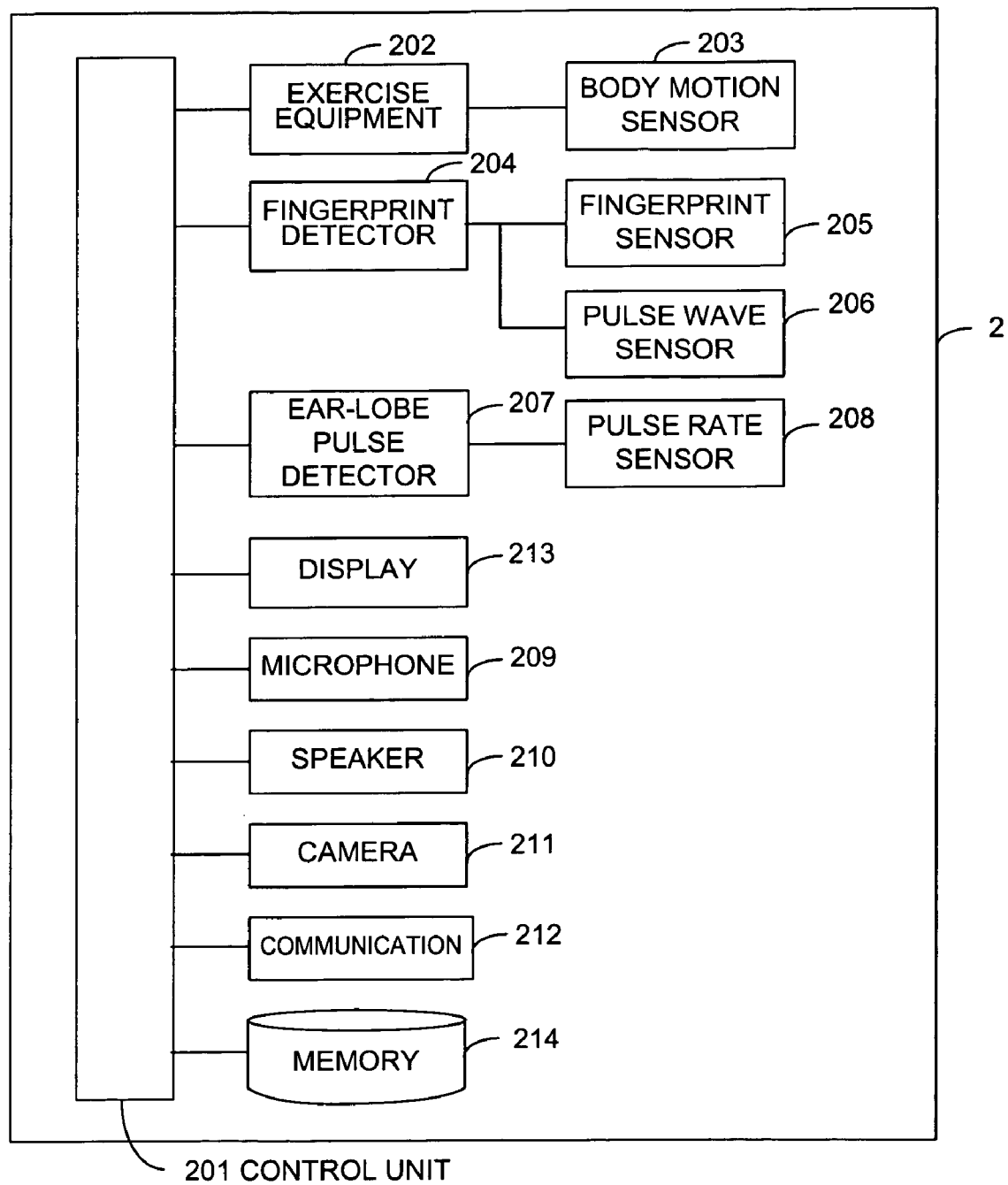
FIG. 12 is a block diagram for showing the control system of the exercise machine of FIG. 11.

FIGS. 11 and 12 show an exercise machine 2 embodying this invention and its control system for not only allowing and/or aiding the user to carry out exercises such as walking, running, rowing, lifting, treading and climbing but also for measuring the user's athletic capabilities in these exercises. For this purpose, the exercise machine 2 comprises a control unit 201 for controlling the overall operations of the exercise machine 2, an exercise equipment 202 such as a tread mill for aiding the user to carry out an exercise, a fingerprint detector 204 for identifying the fingerprints of the user, an earlobe pulse detector 207 for detecting the user's ear-lobe pulse, a display device 213 for displaying various data, a microphone 209 serving as a voice input device, a speaker 210 serving as a voice output device, and a camera 211 for taking pictures of the environment.

The exercise machine 2 further includes a communication interface 212 for communicating with external apparatus, a body motion sensor 203 and a memory 214. The body motion sensor 203 serves to measure the user's body strength such as the maximum amount of exercise per unit time allowable for the user, the maximum allowable pulse rate and the pulse rate when a specified kind of exercise is being done. The memory 214 serves to store the programs to be carried out by the control unit 201 and various other kinds of data including the results of measurements by the exercise machine 2.

The exercise machine 2 also includes a fingerprint sensor 205 and a pulse wave sensor 206. The user's fingerprints are checked by the fingerprint detector 204 on the basis of data detected by the fingerprint sensor 205. The user's pulse waves (the heart beats) are measured on the basis of the detection by the pulse wave sensor 206. It is desirable to place the fingerprint detector 204 at the position where the user's finger will be automatically set when the exercise machine 2 is used, as shown in FIG. 11, such as where the user will most naturally grab the handle. In this manner, the user is not required to go through a special routine to have his/her fingerprints checked. The manner in which the user's fingerprints are analyzed is not different from that for the sphygmomanometer 1 of FIG. 1 and hence will not be explained repetitiously.

The ear-lobe pulse detector 207 is structured so as to be clamped on the ear-lobe of the user. As the user begins his/her exercise with the ear-lobe pulse sensor 207 clamped on the ear-lobe, the pulse data obtained by the ear-lobe pulse detector 207 are used by a pulse rate sensor 208 (shown in FIG. 12) to measure the pulse rate and the pulse waves. The method of measuring the pulse rate is well known and hence will not be presented herein.

The memory 214 serves to store not only the operation program of the exercise machine 2 as a whole but also, like the memory 112 of the sphygmomanometer 1 of FIG. 1, various data including the results of measurement and the user's fingerprint data, although such data may be stored in an external memory device outside the main body of the exercise machine 2 itself. In such a situation, data are communicated from the main body through the aforementioned communication interface 212.

The aforementioned body motion sensor 203 may be replaced by a sensor for detecting the amount of work done by the user such as a device for measuring the distance run by the user as well as the speed of the running motion in the case of a running exercise on a tread mill as shown at 202 in FIG. 11, or both the body motion sensor 203 and such a device may be provided. If specified parameters are used, the calorie expenditure by the user may also be calculated from the measured body motion by such a device or devices. In what follows, the expression "body motion sensor" will be used broadly, inclusive of functions of measuring the traveled distance and speed.

FIG. 13 shows an example of operation program for the exercise machine 2. As in the case of the sphygmomanometer 1 of FIG. 1, it is necessary to ascertain whether or not the exercise machine 2 is going to be used by one of preliminarily registered users. Methods of preliminarily registering users (by their fingerprints) are well known and will not be explained herein. The program shown in FIG. 13 may be retrieved from the memory 214 by the control unit 201.

To start, the fingerprint of the user about to use the exercise machine 2 is examined by the fingerprint detector 204 to determine with reference to data stored in the memory 214 or elsewhere whether or not it is the fingerprint of a preliminarily registered user (Step S201). This may be done automatically as the user grabs the handle of the exercise machine 2 as shown in FIG. 11.

If it is determined that the user is one of preliminarily registered users (YES in Step S203), the user begins an exercise by using the exercise machine 2 (Step S205). The exercise machine 2 may be set in a locked condition from which it can be unlocked only after the user is found to be one of the preliminarily registered users. Alternatively, the exercise machine 2 may be designed such that measurements will not be taken unless the identity of the user is established.

After the user begins to use the exercise machine 2, the fingerprint detector 204 detects and measures the user's pulse waves (Step S207), say, as the user grabs the handle of the exercise machine 2 where the fingerprint detector 204 is set. For the convenience of the description, the pulse wave data obtained in Step S207 are hereinafter referred to as "Pulse Data 1".

At the same time, the ear-lobe pulse detector 207 clamped on the user's ear-lobe serves to detect and measure the user's pulse waves (Step S209). The pulse wave data thus obtained in Step S209 are hereinafter referred to as "Pulse Data 2".

If Pulse Data 1 measured in Step S207 and Pulse Data 2 measured in Step S209 match (YES in Step S211), it is concluded that the user currently using the exercising machine 2 is the same as the preliminarily registered user identified in Step S201, and the use of the exercise machine 2 is continued (Step S213). At the same time, data are obtained by the body motion sensor 203 and, for example, the distance run by the user as well as the speed may be measured. The user's vital capacity and heart beat rate may also be measured. Specified parameters may be used to calculate the calorie consumption by the user.

When a specified time has elapsed or when a specified amount of exercise has been carried out (YES in Step S215), the measured data on the exercise by the user are stored in the memory 214, or transmitted elsewhere through the communication interface 212 (Step S217). The time for exercise and the amount of exercise may be preliminarily inputted through an input device (not shown) or may be automatically set on the basis of the data on the previous use of the exercise machine 2 by the user or the data on the athletic capability of the user based on the user's data over a specified period of time.

If the fingerprints of the user detected in Step S203 do not match the preliminarily registered data (NO in Step S203) or if Pulse Data 1 measured in Step S207 and Pulse Data 2 measured in Step S209 do not match (NO in Step S211), a counter-measure is taken (Step S219) as in Step S110 in the flowchart of FIG. 7 or 8. The examples of the counter-measure to be hereby taken will not be described repetitiously.

If the user decides to continue the exercise even after the predetermined time has elapsed or the specified amount of exercise has been performed (NO in Step S215), the program returns to Step S201 and repeats the subsequent steps thereafter. In this case, the checking of the fingerprints in Steps S201 and S203 may be dispensed with and the program may return to Step S205.

With the exercise machine 2 thus operated, too, the user's identity is checked by way of the fingerprint data to ascertain whether or not the user is preliminarily registered. Since this identity check is carried out by using two sets of pulse data automatically extracted as the user exercises, improper use of the exercise machine 2 can be dependably prevented.

It can still happen that the exercise machine 2 is used by a person different from the person on which Pulse Data 1 and 2 were measured. A variation of the exercise machine 2 in order to more dependably prevent such an improper use by an unauthorized person will be explained next.

The aforementioned variation is similar to the exercise machine 2 described above with reference to FIGS. 11 and 12 but is different therefrom in that the ear-lobe pulse detector 207 and the pulse rate sensor 208 are dispensed with but data on athletic capabilities of individual users are cumulatively stored in the memory 214 or elsewhere connected through the communication interface 212. Such data on each of the individual users may include characteristically his/her own pattern of change in the pulse waves according to the amount of exercise carried out. In general, the pulse waves change with the amount of exercise such that the pulse period becomes shorter and the wave width becomes narrower as the amount of exercise increases. The pattern of these changes, however, is generally different from one individual to another. The pulse rate of a person who takes regular exercises does not change much after a small amount of exercise. The pulse rate of a person who does not exercise regularly, by contrast, will change significantly more even after a small amount of exercise. In this explanation, "pulse waves" are those measured by the fingerprint detector 204, or Pulse Data 1.

FIG. 14 shows an example of operation program for the variation exercise machine described above. The flowchart of FIG. 14 is the same as that of FIG. 13 down to Step S207 but, after Pulse Data 1 are measured in Step S207, the program extracts a past pulse wave pattern of this user from the memory 214 or elsewhere (Step S208). Explained more in detail, the current user's data on his/her athletic capability (or physical condition) are retrieved and a pattern of change in the pulse waves corresponding to the change in the amount of exercise is extracted therefrom. The pattern thus extracted in Step S208 is hereafter referred to as "Pulse Pattern 2".

Thereafter, Pulse Data 1 measured in Step S207 and Pulse Pattern extracted in Step S208 are compared. If they match (YES in Step S212), it is concluded that the current user is the same preliminarily registered user identified in Step S201, and the use of the exercise machine is continued (Step S213). Since Pulse Data 1 and Pulse Pattern 2 may fail to match because of the difference in the body condition of the same user, an exact match need not be required. The definition of a matching condition may be appropriately determined.

If Pulse Data 1 measured in Step S207 and Pulse Pattern extracted in Step S208 are found not to match according to the defined criterion, it is checked whether it was due to an abnormal biological condition of the user (Step S218). If it is so found (YES in Step S218), such information may be communicated to the user through the speaker 210 and/or communicated to a relevant medical institution through the communication interface 212. If it is ascertained that the discrepancy between Pulse Data 1 measured in Step S207 and Pulse Pattern extracted in Step S208 is not because of a particular biological condition of the user (NO in Step S218), the aforementioned counter-measure is taken (Step S219), the detail of which will not be repeated here.

Measured data on the athletic capability of the user as well as the pattern of pulse waves are stored in the memory 214 or transmitted elsewhere through the communication interface 212 (Steps S217 and S220).

If the user decides to continue the exercise even after a predetermined time has elapsed or a specified amount of exercise has been performed (NO in Step S215), the program may return to Step S207, repeating the steps after Step S205, as shown in FIG. 15 which is a variation of the program shown in FIG. 14.

FIG. 15 shows still another program aimed to more dependably prevent an erroneous or fraudulent use of an exercise machine. The flowchart is probably self-explanatory because comparable steps are indicated by same symbols as in FIGS. 13 and 14. According to this program, ear-lobe pulse waves are measured to obtain Pulse Data 1 (Step 209) as shown in FIG. 13 and a past pulse wave pattern of the user ("Pulse Pattern 3") is extracted from the memory 214 or elsewhere (Step 208' which is similar to Step 208 of FIG. 14). The exercise will not be continued unless Pulse Data 1 match both Pulse Data 2 and Pattern 3 (YES both in Steps 211 and 212').

Both FIGS. 14 and 15 show a program in which pulse waves measured by the fingerprint detector 204 (as Pulse Data 1) are compared with the stored pulse wave pattern, but pulse wave data obtained from the ear-lobe pulse sensor may be used instead. Pulse waves obtained by a different sphygmomanometer (not shown) or obtained by some other means may also be substituted.

By any of these variations, it can be dependably checked whether or not the current user is one of preliminarily registered users and this can be done by way of comparing data which are necessarily obtained as the machine is used and data that are already stored. As explained above with reference to the sphygmomanometer 1, the process of identifying the user need not depend on the use of pulse waves but may also depend on the body impedance of the user. The program for identifying the user may be provided in a form readable by a computer such as a flexible disk, a CD-ROM, a ROM, a RAM or a memory card. They may also be provided as recorded on the hard disk of a computer. The program may be provided by downloading through a network and executed after installed on the hard disk. In summary, the disclosure is intended to be interpreted broadly and all modifications and variations of the disclosure that may be apparent to a person skilled in the art are intended to be within the scope of the invention.

What is claimed is:

1. An apparatus for calculating blood pressure by measuring biological data of a user, said apparatus comprising:
    input means for said user using said apparatus to command measurement of said biological data;
    data obtaining means for simultaneously obtaining fingerprint data of said user and a first signal from the body of said user;
    first identifying means for determining whether or not said user is one of registered users by using said fingerprint data;
    measuring means for measuring biological data of said user;
    extracting means for extracting a second signal from said measured biological data of said user;
    calculating means for calculating a blood pressure value from said measured biological data;
    second identifying means for determining whether or not said user is the user identified by said first identifying means by using said first signal obtained by said data obtaining means and said extracted second signal;
    memory means for storing said calculated blood pressure value; and
    output means for outputting said blood pressure value calculated from said measured biological data.

2. The apparatus of claim 1 wherein said second identifying means identifies said user by determining whether or not said first signal matches said second signal.

3. The apparatus of claim 1 wherein said memory means stores said blood pressure value calculated from said measured biological data only if said first identifying means determines that said user is one of registered users and said second identifying means determines that said user from whom said biological data were obtained is the user identified by said first identifying means.

4. The apparatus of claim 1 wherein said first signal and said second signal are pulse wave data of said user.

5. The apparatus of claim 1 further comprising communicating means for transmitting said measured biological data to an external memory means.

6. The apparatus of claim 5 further comprising:

counter-measurement means for taking a counter-measure under at least one of the conditions wherein said first identifying means determines that said user is not one of registered users and wherein said second identifying means determines that said user is not the same as the user identified by said first identifying means; and image taking means;

wherein said counter-measurement means causes said image taking means to obtain an image of at least one selected from the group consisting of said user and an environment over 360 degrees around said measuring means, depending on the identification by said first identifying means or said second identifying means, and said communicating means serves to output said image obtained by said image taking means.

7. The apparatus of claim 1 further comprising counter-measurement means for taking a counter-measure under at least one of the conditions wherein said first identifying means determines that said user is not one of registered users and wherein said second identifying means determines that said user is not the same as the user identified by said first identifying means.

8. The apparatus of claim 7 wherein said counter-measurement means prevents said measuring means from taking said biological data of said user.

9. The apparatus of claim 7 wherein said counter-measurement means outputs results of determination by said first identifying means or said second identifying means.

10. The apparatus of claim 7 further comprising image taking means, wherein said counter-measurement means causes said image taking means to obtain an image of at least one selected from the group consisting of said user and an environment over 360 degrees around said measuring means, depending on the identification by said first identifying means or said second identifying means, and memory means further serving to store said image obtained by said image taking means.

11. The apparatus of claim 7 wherein said counter-measurement means causes said fingerprint data obtained by said data obtaining means to be stored in said memory means if said first identifying means determines that said user is not one of said registered users.

12. The apparatus of claim 1 wherein said biological data includes data on at least one selected from the group consisting of blood pressure and athletic capability of said user.

13. An apparatus for calculating blood pressure by measuring biological data of a user, said apparatus comprising:

data obtaining means for simultaneously obtaining fingerprint data and a first signal from the body of said user;

first identifying means for determining whether or not said user is one of registered users by using said fingerprint data;

measuring means for measuring biological data of said user;

calculating means for calculating a blood pressure value from said measured biological data;

memory means for storing said blood pressure value calculated from said measured biological data and said first signal; and second identifying means for determining whether or not said user from whom said biological data were obtained is the user identified by said first identifying means by using said first signal stored in said memory means and a second signal that is obtained from said user when said biological data of said user are measured by said measuring means.

14. The apparatus of claim 13 further comprising abnormality identifying means for identifying an abnormal biological condition of said user by using said. first signal stored in said memory means and said second signal obtained by said measuring means.

15. The apparatus of claim 13 wherein said second identifying means identifies said user by determining whether or not said first signal matches said second signal.

16. The apparatus of claim 13 wherein said memory means stores said blood pressure value calculated from said measured biological data only if said first identifying means determines that said user is one of registered users and said second identifying means determines that said user from whom said biological data were obtained is the user identified by said first identifying means.

17. The apparatus of claim 13 wherein said first signal and said second signal are pulse wave data of said user.

18. The apparatus of claim 13 further comprising communicating means for transmitting said measured biological data to an external memory means.

19. The apparatus of claim 18 further comprising:

counter-measurement means for taking a counter-measure under at least one of the conditions wherein said first identifying means determines that said user is not one of registered users and wherein said second identifying means determines that said user is not the same as the user identified by said first identifying means; and image taking means;

wherein said counter-measurement means causes said image taking means to obtain an image of at least one selected from the group consisting of said user and an environment over 360 degrees around said measuring means, depending on the identification by said first identifying means or said second identifying means, and said communicating means serves to output said image obtained by said image taking means.

20. The apparatus of claim 13 further comprising counter-measurement means for taking a counter-measure under at least one of the conditions wherein said first identifying means determines that said user is not one of registered users and wherein said second identifying means determines that said user is not the same as the user identified by said first identifying means.

21. The apparatus of claim 20 wherein said counter-measurement means prevents said measuring means from taking said biological data of said user.

22. The apparatus of claim 20 wherein said counter-measurement means outputs results of determination by said first identifying means or said second identifying means.

23. The apparatus of claim 20 further comprising image taking means, wherein said counter-measurement means causes said image taking means to obtain an image of at least one selected from the group consisting of said user and an environment over 360 degrees around said measuring means, depending on the identification by said first identifying means or said second identifying means, and said memory means further serving to store said image obtained by said image taking means.

24. The apparatus of claim 20 wherein said countermeasurement means causes said fingerprint data obtained by said data obtaining means to be stored in said memory means if said first identifying means determines that said user is not one of said registered users.

25. The apparatus of claim 13 wherein said biological data includes data on at least one selected from the group consisting of blood pressure and athletic capability of said user.

26. An exercise machine comprising:
data obtaining means for simultaneously obtaining fingerprint data and a first signal obtained from the body of a user using said exercise machine;
first identifying means for determining whether or not said user is one of registered users by using said fingerprint data;
exercising means for aiding said user to carry out exercises, obtaining exercise data on amount of exercise carried out by said user and a second signal from body of said user and saving said exercise data;
second identifying means for determining whether or not said user from whom said exercise data are obtained is the user identified by said first identifying means by using said first signal obtained by said first identifying means and said second signal obtained by said exercising means together with said exercise data; and
memory means for storing said exercise data.

27. An exercise machine comprising:
data obtaining means for simultaneously obtaining fingerprint data and a first signal obtained from the body of a user using said exercise machine;
first identifying means for determining whether or not said user is one of registered users by using said fingerprint data;
exercising means for aiding said user to carry out exercises, obtaining exercise data on amount of exercise carried out by said user and a second signal from body of said user and saving said exercise data;
memory means for storing said exercise data and said first signal; and
second identifying means for determining whether or not said user from whom said exercise data are obtained is the user identified by said first identifying means by using said first signal stored in said memory means and said second signal obtained by said exercising means together with said exercise data.

* * * * *